(12) United States Patent
Lange et al.

(10) Patent No.: US 9,696,264 B2
(45) Date of Patent: Jul. 4, 2017

(54) APPARATUS AND METHODS FOR DETERMINING DEFECT DEPTHS IN VERTICAL STACK MEMORY

(71) Applicant: KLA-Tencor Corporation, Milpitas, CA (US)

(72) Inventors: Steven R. Lange, Alamo, CA (US); Robert M. Danen, Pleasanton, CA (US); Stefano Palomba, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/226,745

(22) Filed: Mar. 26, 2014

(65) Prior Publication Data

US 2014/0300890 A1   Oct. 9, 2014

Related U.S. Application Data

(60) Provisional application No. 61/807,753, filed on Apr. 3, 2013.

(51) Int. Cl.
*G01N 21/88* (2006.01)
*G01N 21/95* (2006.01)
*G01N 21/17* (2006.01)

(52) U.S. Cl.
CPC ..... *G01N 21/9501* (2013.01); *G01N 21/8806* (2013.01); *G01N 2021/1785* (2013.01)

(58) Field of Classification Search
CPC ............... G01N 21/9501; G01N 21/94; G01N 2021/1785; G01N 21/8806; G02B 21/006

(Continued)

(56) References Cited

U.S. PATENT DOCUMENTS 4,732,473 A   3/1988 Bille et al.
5,248,876 A   9/1993 Kerstens et al.
(Continued)

FOREIGN PATENT DOCUMENTS

EP   0168643 B1   1/1986
EP   1203257 B1   12/2004
(Continued)

OTHER PUBLICATIONS

Author: Pavel et al., Title: Spatial light modulators in fluorescence microscopy, Date: 2010, Publisher: Microscopy: science, Technology, Application and Education.*

(Continued)

*Primary Examiner* — Mark R Gaworecki
(74) *Attorney, Agent, or Firm* — Kwan & Olynick LLP (57) ABSTRACT

Disclosed are methods and apparatus for inspecting a vertical semiconductor stack of a plurality of layers is disclosed. The method includes (a) on a confocal tool, repeatedly focusing an illumination beam at a plurality of focus planes at a plurality of different depths of a first vertical stack, wherein a defect is located at an unknown one of the different depths and the illumination beam has a wavelength range between about 700 nm and about 950 nm, (b) generating a plurality of in-focus images for the different depths based on in-focus output light detected from the first vertical stack at the different depths, wherein out-of-focus output light is inhibited from reaching the detector of the confocal system and inhibited from contributing to generation of the in-focus images, and (c) determining which one of the different depths at which the defect is located in the first vertical stack based on the in-focus images.

22 Claims, 10 Drawing Sheets

(58) Field of Classification Search
USPC .................................................... 250/338.1
See application file for complete search history.

(56) References Cited

U.S. PATENT DOCUMENTS

| | | | | |
|---|---|---|---|---|
| 6,172,349 | B1 * | 1/2001 | Katz | G01B 9/04 250/201.2 |
| 6,248,988 | B1 * | 6/2001 | Krantz | G02B 21/004 250/201.3 |
| 6,548,796 | B1 * | 4/2003 | Silvermintz | G02B 21/0024 250/201.3 |
| 6,674,572 | B1 | 1/2004 | Scheruebl et al. | |
| 7,324,214 | B2 | 1/2008 | Groot et al. | |
| 7,659,975 | B1 | 2/2010 | Ramani et al. | |
| 7,684,049 | B2 | 3/2010 | Groot et al. | |
| 7,715,021 | B2 | 5/2010 | Winterot | |
| 8,194,240 | B1 * | 6/2012 | Vaez-Iravani | G01B 11/0608 356/124 |
| 8,605,275 | B2 * | 12/2013 | Chen | G01N 21/9501 356/237.2 |
| 2002/0188917 | A1 * | 12/2002 | Yokoyama | G01N 21/9501 382/145 |
| 2004/0042001 | A1 * | 3/2004 | Vaez-Iravani | G01N 21/8806 356/237.2 |
| 2005/0036667 | A1 * | 2/2005 | So | G06K 9/00127 382/128 |
| 2005/0134857 | A1 * | 6/2005 | Maury | G01R 31/2831 356/432 |
| 2005/0156098 | A1 * | 7/2005 | Fairley | G01N 21/9501 250/201.3 |
| 2006/0147176 | A1 * | 7/2006 | Takamatsu | G02B 21/14 385/147 |
| 2007/0058164 | A1 * | 3/2007 | Shibata | G01N 21/95607 356/237.2 |
| 2008/0151226 | A1 * | 6/2008 | Hecker | G02B 21/0032 356/73 |
| 2008/0174784 | A1 * | 7/2008 | Colonna De Lega | G01B 9/02057 356/511 |
| 2009/0182528 | A1 * | 7/2009 | De Groot | G01B 11/06 702/167 |
| 2009/0225310 | A1 * | 9/2009 | Yang | G01N 21/658 356/301 |
| 2010/0188742 | A1 * | 7/2010 | Chen | G02B 21/0032 359/385 |
| 2010/0231902 | A1 * | 9/2010 | Markwort | G01N 21/9501 356/237.2 |
| 2011/0109738 | A1 * | 5/2011 | Sakaguchi | G01B 11/02 348/126 |
| 2011/0182496 | A1 * | 7/2011 | Sakai | G01N 21/956 382/145 |
| 2012/0044486 | A1 | 2/2012 | Chen et al. | |
| 2012/0212718 | A1 | 8/2012 | Den Boef | |
| 2012/0224183 | A1 * | 9/2012 | Fay | G01B 9/0209 356/491 |
| 2012/0316855 | A1 * | 12/2012 | Park | G01N 21/9501 703/13 |
| 2013/0114880 | A1 * | 5/2013 | Matsumoto | G01B 11/303 382/149 |
| 2013/0148114 | A1 * | 6/2013 | Berlatzky | G01N 21/956 356/237.5 |
| 2013/0148115 | A1 * | 6/2013 | Berlatzky | G01N 21/956 356/237.5 |
| 2014/0043619 | A1 * | 2/2014 | Deng | G01B 11/24 356/601 |
| 2014/0210983 | A1 * | 7/2014 | Shimura | G02B 21/0016 348/80 |
| 2015/0015874 | A1 * | 1/2015 | Chen | G01N 21/8806 356/237.1 |

FOREIGN PATENT DOCUMENTS

| | | |
|---|---|---|
| WO | 2006048428 A1 | 5/2006 |
| WO | 2010149403 A1 | 12/2010 |
| WO | 2012006221 A1 | 1/2012 |

OTHER PUBLICATIONS

Author: Pavel et al., Title: Spatial light modulators in fluorescence microscopy, Date: 2010, Publisher: Microscopy: Science, Technology, Applications and Education, FORMATEX.*

"International Application Serial No. PCT/US2014/032842, Search Report and Written Opinion mailed Jul. 29, 2014", 12 pgs.

* cited by examiner

APPARATUS AND METHODS FOR DETERMINING DEFECT DEPTHS IN VERTICAL STACK MEMORY

CROSS-REFERENCE TO RELATED APPLICATION

This application claims priority to U.S. Provisional Patent Application No. 61/807,753, filed 3 Apr. 2013, which application is incorporated herein by reference in its entirety for all purposes.

TECHNICAL FIELD OF THE INVENTION

The invention generally relates to the field of wafer and reticle inspection systems. More particularly the present invention relates to inspection and review of vertical memory device structures.

BACKGROUND

As demand for ever-shrinking semiconductor devices continues to increase, it has become particularly difficult to continue shrinking semiconductor devices, such as memory, due to rapidly increasing costs associated with lithography and multiple process steps associated with pitch splitting techniques.

Vertical memory, such as 3D or vertical NAND (VNAND) memory, appears to be a promising direction for increasing memory density. Implementation of 3D or VNAND includes building transistors (bits) vertically, rather than orienting memory structures in a planar manner. Early VNAND devices have 16 to 24 vertical bits with future plans to vertically extend to 48 and 64 bits or more. These changes are achieved with fewer process steps, relaxed lithography sizes, and lower manufacturing costs, as compared with the planar approach.

Various inspection systems are used within the semiconductor industry to detect defects on a semiconductor reticle or wafer. However, there is a demand for improved semiconductor wafer inspection systems for implementation with vertical semiconductor devices, such as 3D or VNAND memory or other vertical stacks.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a method for inspecting a vertical stack of a plurality of layers is disclosed. The method includes (a) on a confocal tool, repeatedly focusing an illumination beam at a plurality of focus planes at a plurality of different depths of a first vertical stack, wherein a defect is located at an unknown one of the different depths and the illumination beam has a wavelength range between about 700 nm and about 950 nm, (b) generating a plurality of in-focus images for the different depths based on in-focus output light detected from the first vertical stack at the different depths, wherein out-of-focus output light is inhibited from reaching the detector of the confocal system and inhibited from contributing to generation of the in-focus images, and (c) determining which one of the different depths at which the defect is located in the first vertical stack based on the in-focus images.

In a specific implementation, the wavelength range is an infrared and/or near infrared range. In one example, the out-of-focus light is inhibited from reaching the detector of the confocal tool by an output aperture module that is positioned and dimensioned so as to block the out-of-focus output light at the wavelength range between about 700 nm and about 950 nm from reaching the detector. In another aspect, the defect was detected in the vertical stack using another inspection tool that differs from the confocal tool, wherein such defect was detected without determining a depth of such defect with respect to the vertical stack.

In a further aspect, the method includes detecting the defect based on the in-focus images prior to determining which one of the different depths at which the defect is located in the first vertical stack based on the in-focus images. In another aspect, determining which one of the different depths at which the defect is located in the first vertical stack includes determining that a particular one of the in-focus images has a sharpest contrast and defining the particular in-focus image's corresponding depth as the depth of the defect. In another embodiment, the method includes determining a classification of the defect or discriminating a material of the defect based on the in-focus images.

In another embodiment, the invention pertains to an apparatus for detecting defects or reviewing defects in a vertical semiconductor structure. The system includes an illumination optics module for repeatedly focusing an illumination beam at a plurality of focus planes at a plurality of different depths of a first vertical stack. The illumination beam has a wavelength range between about 700 nm and about 950 nm. A defect is located at an unknown plane in one of the different depths. The system also includes a collection optics module for collecting in-focus output light from the plurality of different depths in response to the illumination beam focused at such different depths and a detector for detecting the in-focus output light collected from the plurality of different depths. The collection optics module is further arranged to inhibit out-of-focus output light from reaching the detector so as to inhibit such out-of-focus output light from contributing to generation of the in-focus images. The system further comprises a controller operable to perform the following operations: (i) generating a plurality of in-focus images for the different depths based on in-focus output light detected from the first vertical stack at the different depths, and (ii) determining which one of the different depths at which the defect is located in the first vertical stack based on the in-focus images. In a specific implementation, the system is in the form of a confocal review module for reviewing defects, and the system further comprises an inspector module for detecting defects using a non-confocal inspection mode.

In a specific implementation, the illumination optics module includes an illumination aperture module and the collection optics module includes an output aperture module. In another implementation, each of the illumination and output aperture modules is in the form of a fixed pinhole or slit array. In a further aspect, each of the illumination and output aperture modules is in the form of a rotating Nipkow disk for scanning the focused illumination beam across a focal plane area of the sample. In one embodiment, each of the illumination and output aperture modules is in the form of a programmable spatial modulator for scanning the focused illumination beam across a focal plane area of the sample. In one embodiment, the output aperture module is positioned and dimensioned so as to block the out-of-focus output light at the wavelength range between about 700 nm and about 950 nm from reaching the detector.

In one aspect, the input and output aperture modules are physically the same, for example, so that input light travels through the aperture, slit or SLM from one direction and returns from the other direction before an optical element redirects the return light to the detector. In another embodiment, the illumination optics module includes one or more galvanic mirrors for scanning the focused illumination beam across a focal plane area of the sample. In a specific example, the wavelength range is an infrared and/or near infrared range. In a further aspect, the defect was detected in the vertical stack using another inspection tool that differs from the confocal tool, and such defect was detected without determining a depth of such defect with respect to the vertical stack. In this embodiment, the same or another set of one or more galvanic mirrors scans the in-focus output light onto the detector.

In a specific embodiment, the controller is further operable to detect the defect based on the in-focus images prior to determining which one of the different depths at which the defect is located in the first vertical stack based on the in-focus images. In one aspect, determining which one of the different depths at which the defect is located in the first vertical stack includes determining that a particular one of the in-focus images has a sharpest contrast and defining the particular in-focus image's corresponding depth as the depth of the defect. In another aspect, the controller is further operable to determine a classification of the defect or discriminate a material of the defect based on the in-focus images.

These and other aspects of the invention are described further below with reference to the figures.

DETAILED DESCRIPTION OF EXAMPLE EMBODIMENTS

In the following description, numerous specific details are set forth in order to provide a thorough understanding of the present invention. The present invention may be practiced without some or all of these specific details. In other instances, well known component or process operations have not been described in detail to not unnecessarily obscure the present invention. While the invention will be described in conjunction with the specific embodiments, it will be understood that it is not intended to limit the invention to the embodiments.

Although inspection systems and techniques are described herein as being applied to certain types of vertical NAND (VNAND) memory structures, it is understood that embodiments of the present invention may be applied to any suitable 3D or vertical semiconductor structures, such as NAND or NOR memory devices formed using terabit cell array transistors (TCAT), vertical-stacked array transistors (VSAT), bit cost scalable technology (BiCST), piped shaped BiCS technology (P-BiCS), etc. The vertical direction is generally a direction that is perpendicular to the substrate surface. Additionally, although particular fabrication steps, processes, and materials are described for forming such 3D structures, inspection embodiments may be applied at any point in the fabrication flow that results in multiple layers being formed on a substrate, and such layers may include any number and type of materials.

General fabrication techniques for forming vertical structures, such as VNAND, will be described prior to describing various inspection systems and techniques embodiments of the present invention. Specific fabrication details and material types and characteristics are omitted for clarity purposes.

Figure 1A:
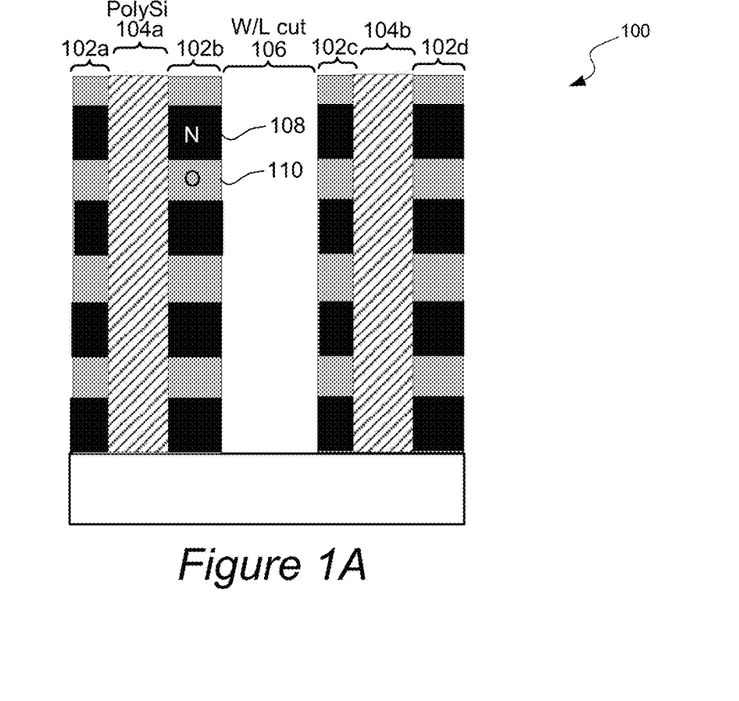
FIGS. 1A-D illustrates a process for fabricating a "gate last" type of vertical NAND (VNAND) memory devices.

FIGS. 1A-D illustrates a process for fabricating a "gate last" type of vertical NAND (VNAND) memory device. This gate last architecture may generally include alternating layers of oxide and SiN or nitride materials, which are collectively referred to as an oxide-nitride-oxide-nitrite (ONON) structure. FIG. 1A is a diagrammatic side view of the patterned ONON layers of a gate last VNAND memory portion 100. As shown, alternating layers of an oxide (O) and nitride (N) material are patterned into ONON stacks 102a, 102b, 102c, and 102d. For instance, stack 102b includes oxide (O) layer portion 110 and nitride (N) layer portion 108. The ONON stacks may be formed by any suitable deposition and etching process so as to form the ONON stacks, as well as the W/L (word-line) cuts (e.g., 106) and vias (e.g., 104a and 104b). The vias may be filled with a polysilicon (PolySi) material. As shown, polysilicon (PolySi) may also be deposited and etched to fill vias or channels 104a and 104b between sets of ONON stacks.

Figure 1B:
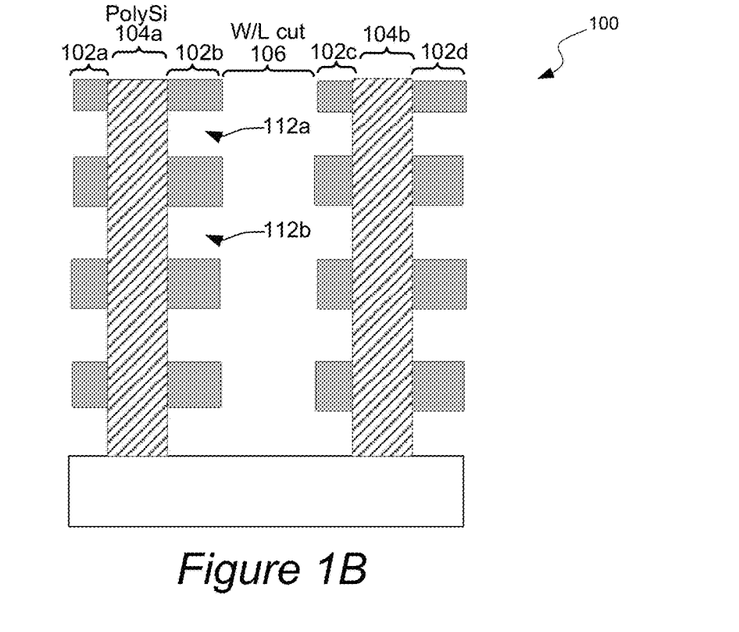
Figure 1C:
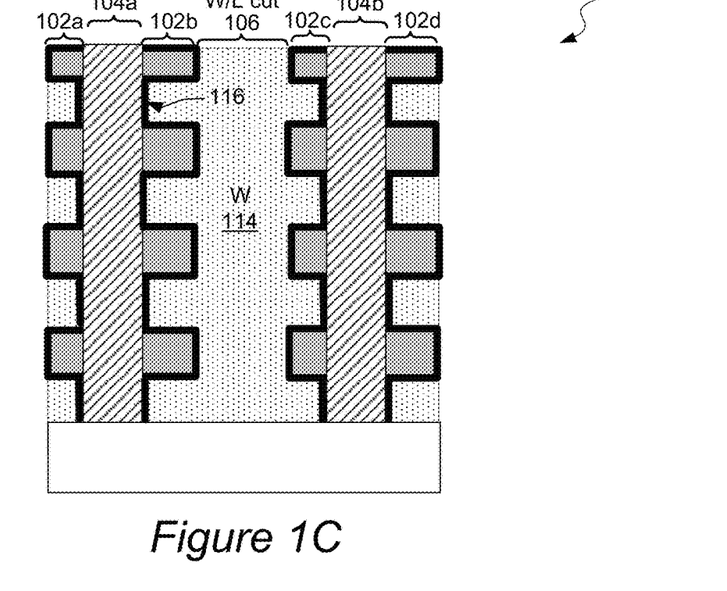
Figure 1D:
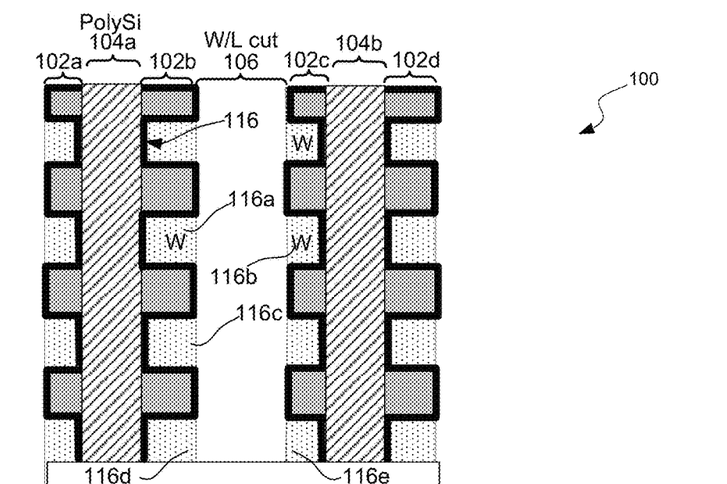

FIG. 1B illustrates the gate last VNAND portion 100 after removal of the nitride material, for example, from areas 112a and 112b. For example, the nitride material may be removed using a wet etch process. FIG. 1C illustrates the VNAND portion 100 after a gate material, e.g., tungsten (W) 114, has been deposited. A dielectric layer 116 is also deposited. The W and dielectric materials are formed within the spaces from which the nitride was previously etched. That is, the nitride material is replaced by the W material. FIG. 1D shows the VNAND portion 100 after the W material is etched back so as to form isolated gate portions, such as 116a, 116b, 116c, 116d, and 116e. The W/L cuts may also be filled with any suitable conductive material (not shown).

Vertical memory devices tend to have thicker stacks of materials and structures, as compared with planar memory devices. For instance, early VNAND devices have 2-3 μm thick stacks, and future stacks are predicted to be in the 6-8 μm range. Some stacks can easily include 60 to 90 layers at varying thicknesses. In comparison, a typical planar memory thickness is about 0.1 to 1 μm, depending upon the process step.

Figure 1E:
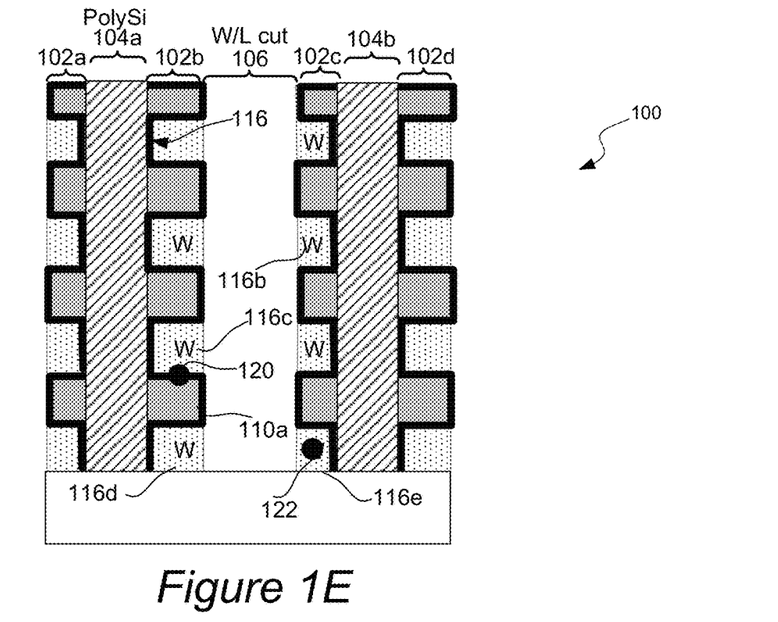
FIG. 1E illustrates the VNAND structure portion of FIG. 1D with defects present in its stack.

Defects can occur throughout layers of these stacks and need to be detected to ensure high manufacturing yields. FIG. 1E illustrates the VNAND structure portion 100 of FIG. 1D with defects present in its stack. As shown, a defect 120 is present at the interface between W gate portion 116c and O portion 110a, while another defect 122 is present in gate portion 116e. Defects, including particles or voids, may be present in any W gate portion, O portion, or interface there between.

Figure 1F:
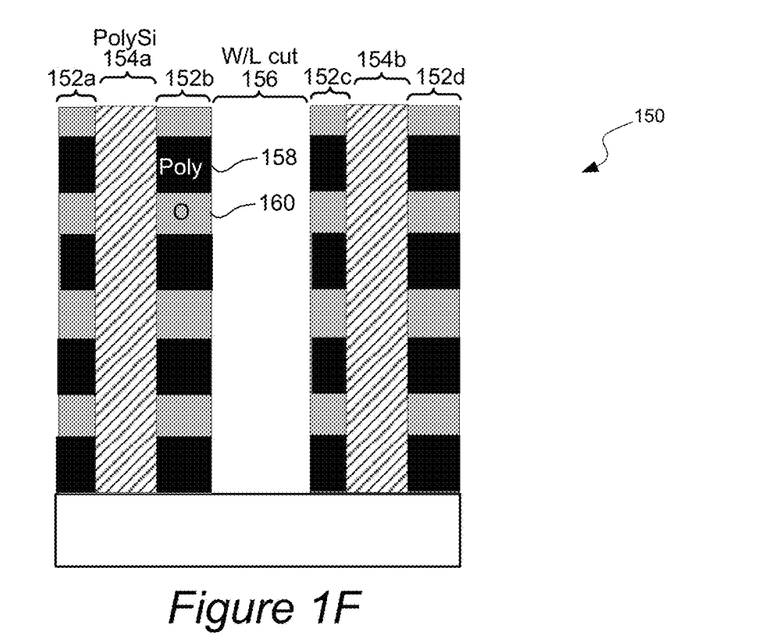
FIG. 1F is a diagrammatic side view of a gate first type of VNAND structure.

FIG. 1F is a diagrammatic side view of a gate first type of VNAND structure. As shown, a gate first VNAND portion may be formed by depositing alternating oxide (O) and poly silicon (Poly Si) layers, which are patterned into stacks 152a, 152b, 152c, and 152d. For example, stack 152b includes poly silicon (poly) gate portion 158 and oxide (O) portion 160. This type of VNAND is referred to as a OPOP VNAND memory device. The VNAND portion 150 may also include Poly Si channels (or other channel materials) 154a and 154b, as well as W/L cut area 156. Defects may be present at any of the levels of the OPOP structure. For instance, particles or voids may be present in any of the layers of an OPOP structure.

Regardless of the particular type of fabrication process, defects need to be detected in all levels of a multiple layer stack and as early as possible in the particular process. Certain inspection embodiments preferably include detection of defects throughout a stack, including the stack surface and throughout the various depths of a stack. For example, certain embodiments allow defects to be found at depths of up to about 3 μm. In another embodiment, defects can be detected at stacks depths that are as large as about 8 μm. Transmission through an ONON or OPOP stack is not limited by absorption at the longer wavelengths, so there is no real limit to the thickness of the vertical ONON or OPOP stack that can be theoretically inspected.

Figure 1G:
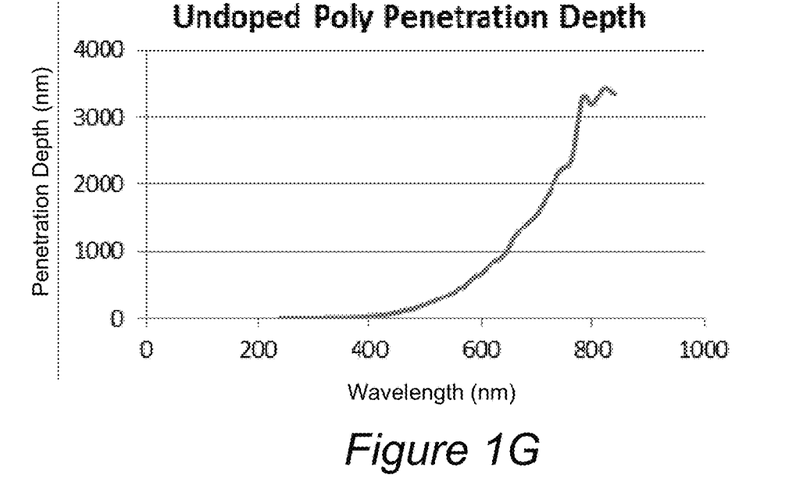
FIG. 1G shows the penetration depth for undoped Poly Si as a function of wavelength.

FIG. 1G shows the penetration depth for undoped Poly Si as a function of wavelength. Certain embodiments of the invention can use higher wavebands to view increased depths of the Poly Si (e.g., of an OPOP structure), as well as other types of stacks. The OPOP layers can be inspected prior to formation of other structures, such as the W/L trenches, of the VNAND device, as well as after formation of other structures, such as the W/L trenches.

An OPOP structure may be difficult to penetrate with shorter wavelengths during an inspection process. Poly Si is quite opaque for wavelengths below 450 nm and gradually becomes more transparent at longer wavelengths. During inspection, light ideally needs to have long enough wavelengths to penetrate the stack of Poly Si and reach a particular defect location and result in light reflected or scattered from the defect being able to penetrate back through the stack of Poly Si to be detected. In sum, longer wavelengths can be used to reach and detect defects that are located deep within an OPOP stack. For an ONON stack, on the other hand, all of the materials are transparent above about 240 nm.

Bright Field (BF) tools typically are able to detect defects of a 3D stack that are either on the surface or covered by a very thin film. The BF tool can detect undersurface defects only when they are closer to the surface or they generate bumps in the stack that can propagate to the surface and, therefore, create a detectable surface defect. These tools detect all the focused and defocused light from the specimen, which prevents the localization of a specific focal plane. The latter is due to the absence of confocal capabilities and the usage of light at very short wavelengths, which do not easily penetrate into materials.

Certain embodiments of the present invention include use of a confocal microscopy system or module to detect defects at various depths in a multiple layer semiconductor stack, such as a VNAND structure. For example, any suitable confocal system may be configured for inspecting 3D stacks. In general, the confocal system is configured to operate at long wavelength ranges, such as visible to near infrared (NIR) or about 700 nm to about 950 nm. In another embodiment the confocal system is configured to operate at shorter wavelengths above 220 nm, for example but not limited to ONON stacks. In other embodiments, an inspection system for inspecting wafers or the like in other inspection modes can include a confocal module for detecting and/or reviewing defects in 3D stacks.

In general, a confocal inspection tool may include at least one light source for generating an illumination light beam at longer wavelengths to detect defects at various depths of a vertical semiconductor stack, an illumination optics module for directing the illumination beam to the stack, a collection optics module for directing in focus output light, while inhibiting or blocking out-of-focus output light, that is emitted from the stack in response to the illumination beam, a detector or sensor for detecting an output beam and generating an image or signal for the output beam, and a controller for controlling the components of the inspection/review tool and facilitating defect detection and/or review based on images generating for various depths in the stack as described further herein.

Figure 2:
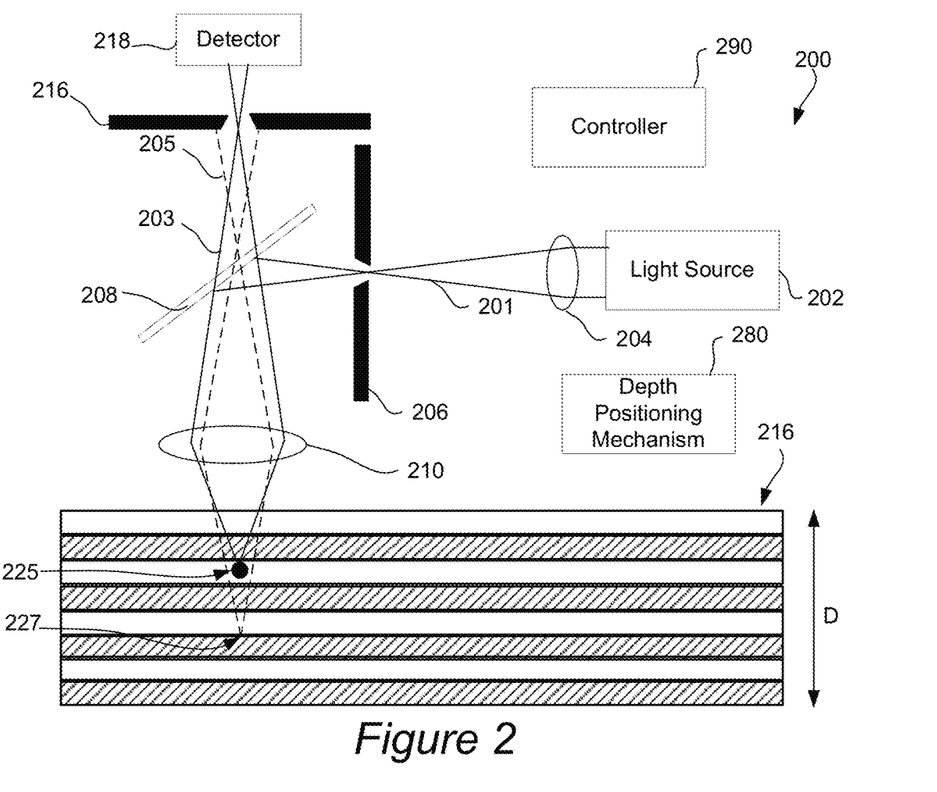
FIG. 2 is a diagrammatic representation of an example inspection or review apparatus in accordance with a specific implementation of the present invention.

FIG. 2 is a diagrammatic representation of an example inspection or review apparatus 200 in accordance with a specific implementation of the present invention. As shown, the system 200 may include one or more light sources, such as a wavelength tunable laser 202, for generating light in a visible, IR, and/or NIR wavelength range. For instance, the light source outputs illumination light at a range between about 700 nm and 950 nm so as to penetrate a 3D stack. Examples of light sources include a laser-driven light source, a high-power plasma light source, a transillumination light source (e.g., halogen or Xe lamp), a filtered lamp, LED light sources, etc. Multiple LED or speckle buster laser diodes are also possible sources.

The system includes illumination optics to direct the illumination light generated by light source 202 towards the sample 216. For example, the illumination from the light source may also pass through a number of lenses which serve to relay (e.g., shape, focus or adjust focus offset, filter/select wavelengths, filter/select polarization states, resize, magnify, reduce distortion, etc.) the beam towards the sample 216. As shown, illumination light 201 is focused by lens 204 through an illumination aperture module 206 onto a beam splitter 208, such as a dichroic mirror, which reflects the illumination light 201 towards the sample 216 via optical lens system 210, which is configured to focus the illumination light 201 from the aperture module 206 onto a focus point or spot, e.g., 225, of the sample 216 that is positioned at a particular depth within the stack.

Focused output light 203 from the focus point 225 is directed back through lens 210 and beam splitter 208. Additionally, unfocused light 205 from unfocused points, e.g., 227, which are positioned at different depths within the stack than the focused spot, is also directed back through lens 210 and beam splitter 208. An output aperture module 216 is positioned and dimensioned so as to pass the focused light 203 and block the unfocused light 205. Accordingly, the focused light 203 can reach detector 218, while the unfocused light 205 is largely blocked from reaching the detector 218.

In general, each optical element of the confocal system or module may be optimized for the longer wavelength range of the light for detecting defects at various depths in 3D stack. Optimization may include minimizing wavelength-dependent aberrations, for example, by selection of glass type, arrangement, shapes, and coatings (e.g., anti-reflective coatings, highly reflective coatings) for minimizing aberrations for the corresponding wavelength range. For example, the lenses are arranged to minimize the effects caused by dispersion by longer wavelength ranges (visible~NIR).

The beam splitter 208 may be coated or formed with any suitable material for reflecting and passing longer wavelengths for penetrating 3D stack structures. Example materials for working with light in the NIR range include most common optical glass materials such as BK7 or Fused Silica, etc. The objective lens 210 is preferably optimized for all of the wavelengths that are used for defect detection. For instance, the objective 210 has a composition, including lens coatings, and arrangement for correction of color aberration. In an alternative embodiment, the objective lens 210 may be an all reflective objective or refractive or a combination (catadioptric) configuration.

The illumination aperture module 206 and the output aperture module 216 are each illustrated as a single aperture for ease of discussion. However, each aperture module may be a single pinhole/slit, pinhole array, slit array, etc. Example aperture modules include a fixed pinhole/slit array, a rotating Nipkow disk, a programmable spatial light modulator (SLM), etc. Different types of confocal systems are contemplated herein. Example confocal systems include confocal laser scanning microscopes, spinning-disk (Nipkow disk) confocal microscopes, and Programmable Array Microscopes (PAM).

Each aperture or slit may be formed from a hole/slit-shaped material that is transparent to longer wavelengths or a hole/slit opening in an opaque mask material. Multi-hole/slit aperture modules can be used to simultaneously direct multiple spots towards the sample and detect multiple spot images of different areas and/or depths of the sample.

The apertures/slits of the aperture modules 206 and 216 are dimensioned to each have a size that is equal to or less than the diffraction limit of the radiation. The apertures may be separated from each other by at least several times the diffraction limit to minimize generation of stray radiation and cross-talk between spots. In one example, the diffraction limit of light with a wavelength of about 700 nm for an illumination lens with a numerical aperture (NA) of 0.90 is approximately 0.80 µm, so that round pinholes having a diameter of 0.60 um would provide adequately small apertures for such lenses (as adjusted for the magnification of the objective lens 210). The detector would also preferably include sensors that are each sized to detect light in an area that is less than or equal to the pinhole area. The pinholes and sensors could also be separated by a distance of 5 um so as to minimize cross-talk.

Referring back to FIG. 2, the inspection system 200 may also include a positioning mechanism 280 for moving the depth position of the focus spot(s) relative to the sample 216, for example, in direction D. That is, the positioning mechanism 280 can control the focus depth of the focus spot(s) within a multiple-layered stack of the sample. For instance, the positioning mechanism may be coupled to the stage (not labelled) for moving the sample 216 so that the focus spot(s) penetrate to different depths of the sample stack 216. Alternatively or additionally, the optics may be moved by a positioning mechanism so as to move the focus spots relative to the sample. Different depths for each simultaneously generated focus spot may also be achieved by tilting an aperture array (and corresponding output aperture array) relative to the sample or tilting the sample relative to the aperture modules.

Several aperture module arrangements and configurations, as well as confocal system configurations, are described further in U.S. Pat. No. 5,248,876, issued 28 Sep. 1993 by Kerstens et al., which patent is incorporated herein by reference for the purpose of various different confocal systems that can be configured for implementing the techniques of the present invention.

The confocal inspection system 200 may also include one or more scanning mechanisms for scanning the focus spot(s) across a focal plane that is parallel to a surface of the sample. In a single aperture implementation, a scanning module (e.g., a set of galvanic mirrors) may be used to scan and detect a focus spot in the focal plane. In another embodiment, each aperture module is in the form of a SLM that is programmed to provide a moving aperture that causes a focus spot to be scanned and detected across the focal plane. An SLM may be programmed to provide any scan pattern, such as raster, spiral, etc. In an alternative embodiment, each aperture module is in the form of a spinning aperture disk that is programmed to provide a moving aperture for rotating and detecting a focus spot in the focal plane.

One or more positioning mechanisms may also be configured to move other components of the inspection system, such as the aperture modules, illumination or collection mirrors, wavelength filters, polarizers, etc. By way of specific examples, one or more motor mechanisms may each be formed from a screw drive and stepper motor, linear drive with feedback position, or band actuator and stepper motor.

Any suitable detector type or number of detection elements may be used to receive the output light from one or more focus spots and provide an image or a signal based on the characteristics (e.g., intensity) of the received output light. By way of example, detector 218 may be in the form of a CCD (charge coupled device) or TDI (time delay integration) detector, photomultiplier tube (PMT), or other sensor (or sensor array). In one embodiment, the detector is an array of isolated point detectors that sense radiation in an area that is also approximately the size of or smaller than the diffraction limit of the radiation to efficiently sense the focused radiation while minimizing detection of unfocused light.

The system also includes one or more controller or computer system modules, e.g., 290, for controlling various components of the system and receiving and analyzing detected signals or images from the detector 218. For instance, the controller may control selective activation of the illumination source, the illumination or output aperture settings, wavelength band, focus offset setting, polarization settings, etc.

Additionally, the signals captured by the detector can be processed by controller 290, which may include a signal processing device having an analog-to-digital converter configured to convert analog signals from each sensor into digital signals for processing. The controller 290 may be configured to analyze intensity, phase, and/or other characteristics of the sensed light beam.

This or any other confocal system may be used to find or review detected defects that are embedded in a 3D stack, such as 3D or VNAND memory structures. Other types of stack structures that may be inspected or imaged using the inspection apparatus of the present invention include solar panel structures, optical disks, etc.

Figure 3A:
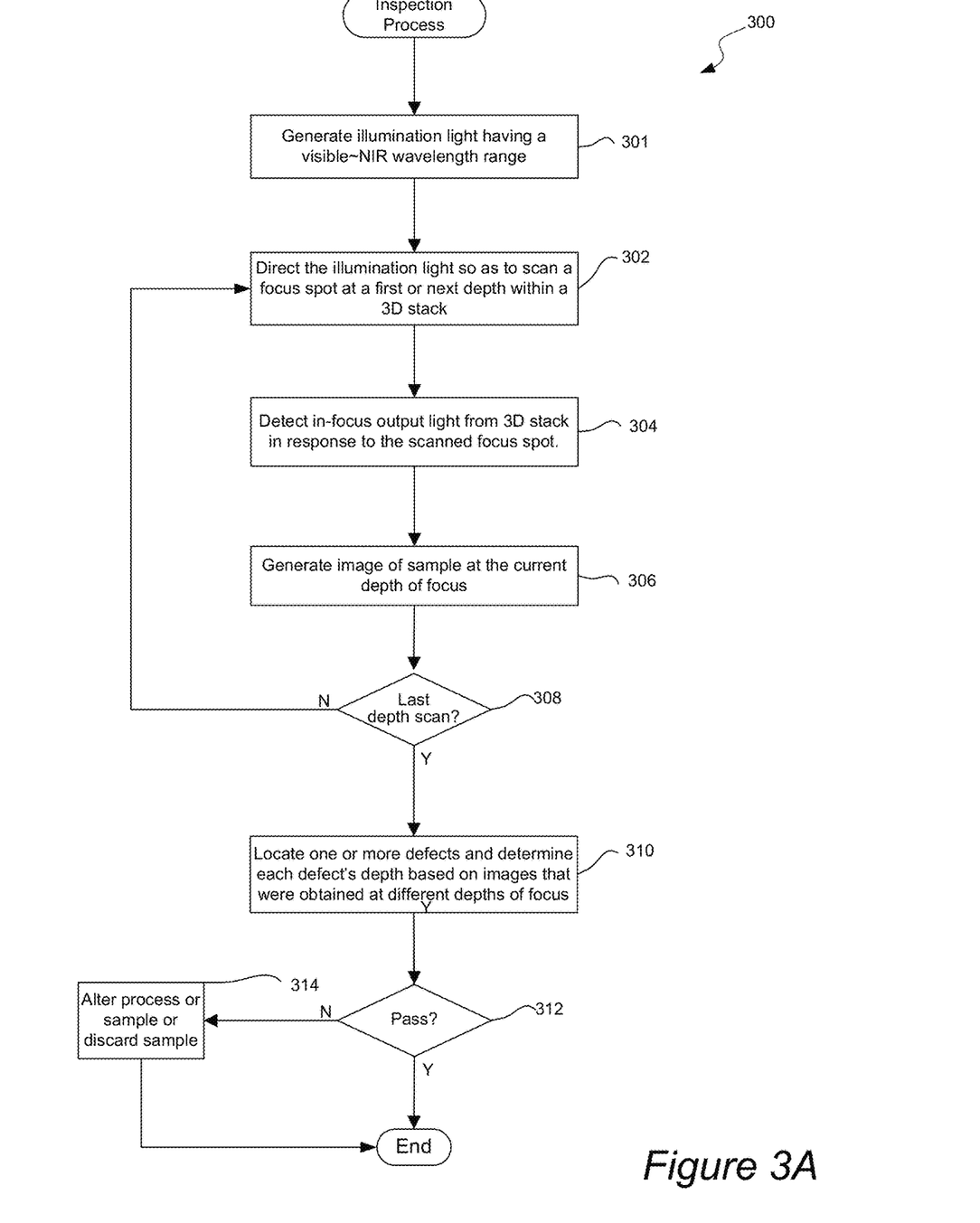
FIG. 3A is a flow chart illustrating an inspection process in accordance with one embodiment of the present invention.

FIG. 3A is a flow chart illustrating an inspection process 300 in accordance with one embodiment of the present invention. Initially, illumination light having a wavelength range between visible and NIR may be generated in operation 301. The illumination light may then be directed so as to scan a focus spot at a first depth within a 3D stack in operation 302. For example, a focus spot is scanned across a portion of the sample at a particular depth of focus. Alternatively, multiple spots may be scanned simultaneously at the same or different depths.

The in-focus output light reflected or scattered from the 3D stack in response to the scanned focus spot may then be detected in operation 304. Alternatively, output light from multiple focused spots may be detected if multiple spots are directed at the sample. An image of the sample at the current depth of focus may also be generated based on the detected in-focus output light in operation 306. If multiple spots are scanned across the sample, the output light that is detected from these multiple spots may be used to generate an image of the scanned sample depth. If multiple spots are simultaneously scanned at different depths of the sample, different images corresponding to the different depths may be individually generated for the different spots.

It may then be determined whether this is the last depth that is to be scanned in operation 308. For instance, the depth of the 3D stack that is to be scanned is known and the depth of focus can be incremented from a top surface of the 3D stack to a bottom of the 3D stack. When the bottom is reached, the scans are complete. Additionally, multiple 3D stack structures can each be scanned at multiple depths of focus, and when the depths of each of the 3D stack structures have been incrementally scanned, the scans are complete. If the scans are not complete, one or more focus spot(s) at a next depth of focus may be scanned and detected and used to generate corresponding detection images at the various depths by repeating operations 302, 304, and 306.

If scans at all the desired depths are complete, one or more defects may be located and each defect's depth may be determined based on the images that were obtained at the different depths of focus in operation 310. In one embodiment, any suitable inspection analysis process may be performed to first find defects. Another non-confocal inspection tool may have been used to detect defects. Alternatively, the confocal tool may be used to find defects based on the images from each depth of focus. For instance, a cell-to-cell, die-to-die, or die-to-database comparison can be made between each test and reference image. For example, defects may be detected for an imaged area at a particular depth that differs from another reference image area at the same depth, which is obtained from another die, cell, or simulated from a design database.

If a defect is found, the depth of the defect may be correlated to the image that has the sharpest contrast for such defect. For instance, the defect will tend to have a maximum brightness (or darkness) as compared to the surrounding background in the image that is generated from the depth of focus that corresponds to such defect's depth within the sample. Accordingly, the center of the depth of focus that was used to generate the image with the highest brightness level for the defect can be defined as the defect's depth. Additionally, the defect's depth may be correlated with known signals from a set of reference defects to determine the defect classification or to discriminate material type. For instance, reference surface defects having known classification and composition may be used to classify the defect or discriminate the material.

The confocal images for a particular stack area can be scanned to find the image in which the defect has the strongest peak. The xy location in the image can be defined as the defect's pixel location. The depth for the defect can be determined by the corresponding z position of the confocal illumination system. The sample's surface relative to the confocal illumination system or stage can be found by moving through the z or focus positions to find the surface, at which there will be a smaller intensity peak.

Figure 3B:
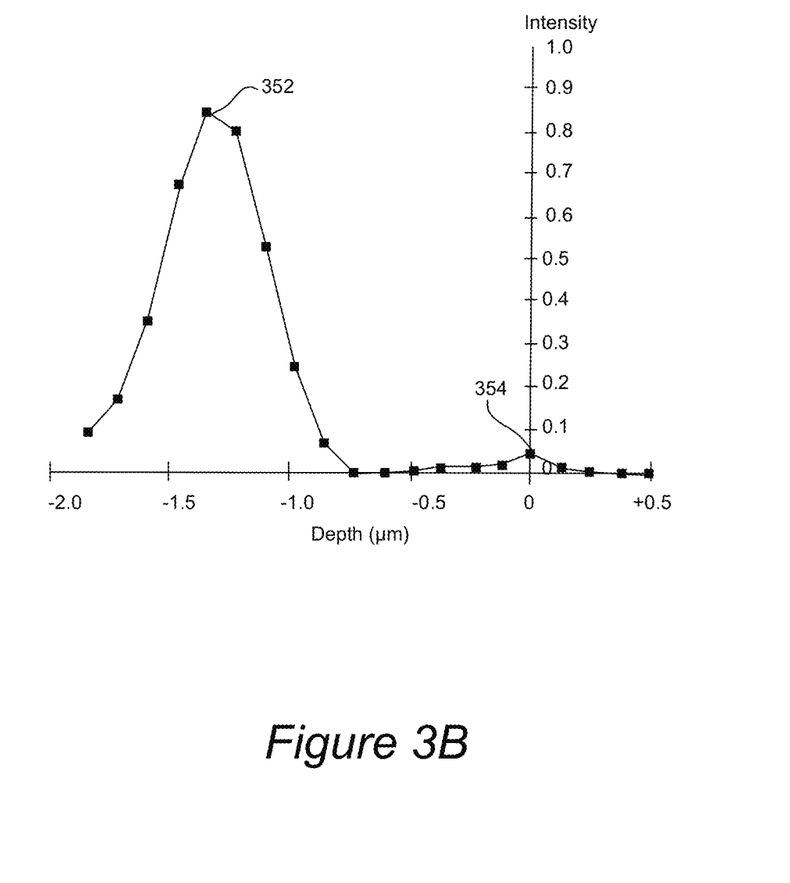
FIG. 3B illustrate a plot of intensity as a function of stack depth for a particular defect's xy position.

FIG. 3B illustrate a plot of intensity as a function of stack depth for a particular defect embedded at a particular depth in a stack. Intensity point 352 corresponds to the highest intensity peak within the confocal images, which gives a depth of about −1.3 µm below the surface. It is noted that the surface depth of 0 corresponds to a small intensity peak 354, while most of the other depths are out of focus and have relatively low intensity values. In this graph, intensity values have been scaled 0 to 1.0, but could be plotted with any suitable metric such as grayscale level (e.g., 0-255). With the exception of the surface, signals from regular wafer patterns that repeat at multiple depths have been removed from the graphs in FIG. 3B by using confocal images at a particular depth from a non-defective but otherwise similar region on the wafer.

Referring back to FIG. 3A, it may then be determined whether the sample has passed inspection in operation 312 after each defect is reviewed at its corresponding depth. For instance, it may be determined whether the defects are yield-limiting defects or merely nuisance type defects. It may also be determined whether the defect is repairable. If the sample does not pass, the process or sample may be altered in operation 314. The sample may also be discarded, in addition to altering the process.

Figure 4:
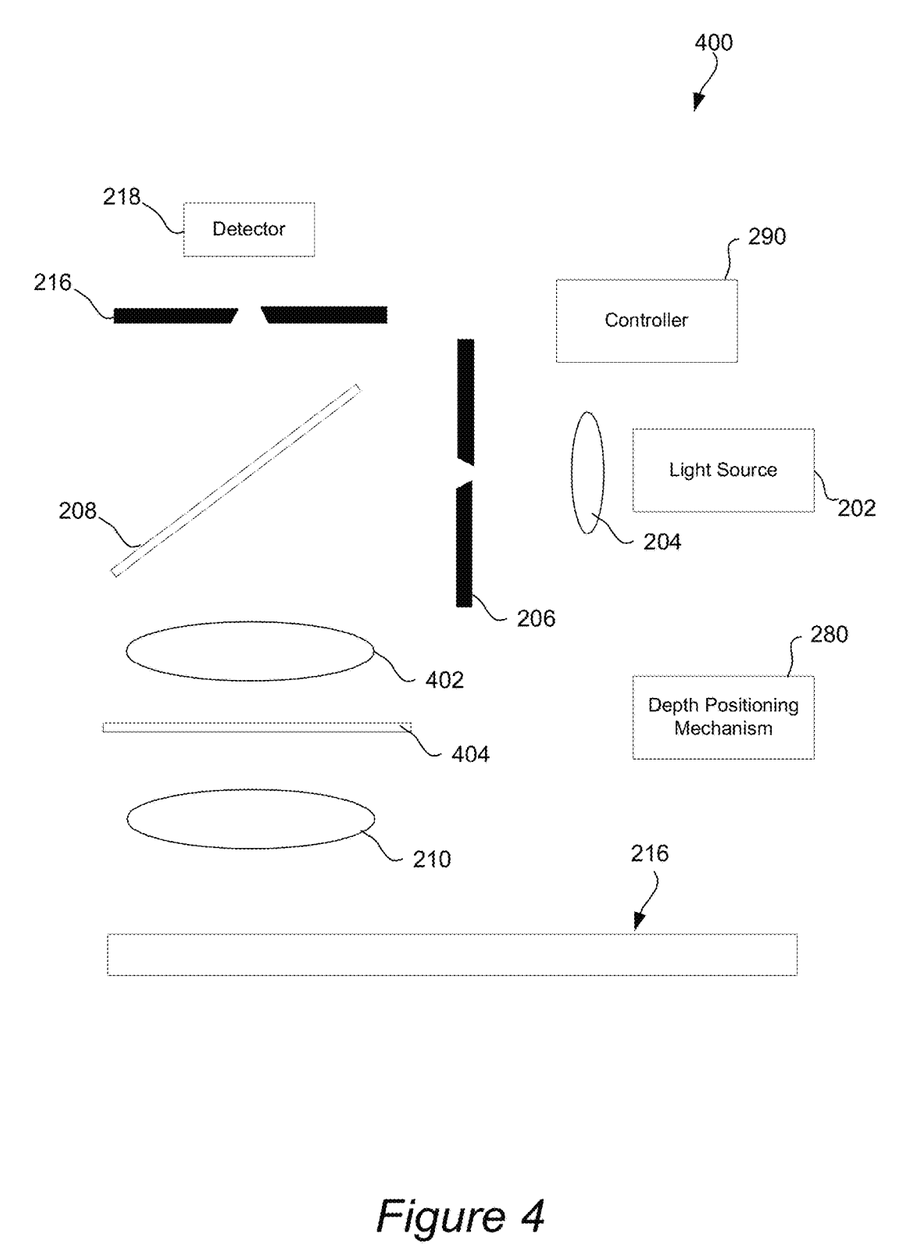
FIG. 4 is a diagrammatic representation of a confocal inspection system that includes sub-band filters in accordance with an alternative embodiment.

FIG. 4 is a diagrammatic representation of a confocal inspection system 400 that includes sub-band filters in accordance with an alternative embodiment. This system is similar to the system of FIG. 2 with the addition of a tunable or selectable spectral filter 404 that is configurable to increase sensitivity for particular materials and stack types. A spectral filter may be used to further dynamically define the spectrum of the illumination beam.

One or more spectral sub-band filters may be placed in an illumination pupil of the illumination beam to achieve different sub-band wavelength ranges. As shown, a spectral sub-band filter 404 is placed between objective 406 and collimator lens 402. However, the system may include any number and type of lenses for forming an illumination pupil at which a spectral sub-band filter may be positioned.

The confocal techniques described herein can be combined with other techniques, such as fluorescence and multiphoton detection, in which the light detected from the buried defect is at longer or shorter wavelength when the specimen is illuminated at different wavelengths, respectively shorter and longer.

Figure 5:
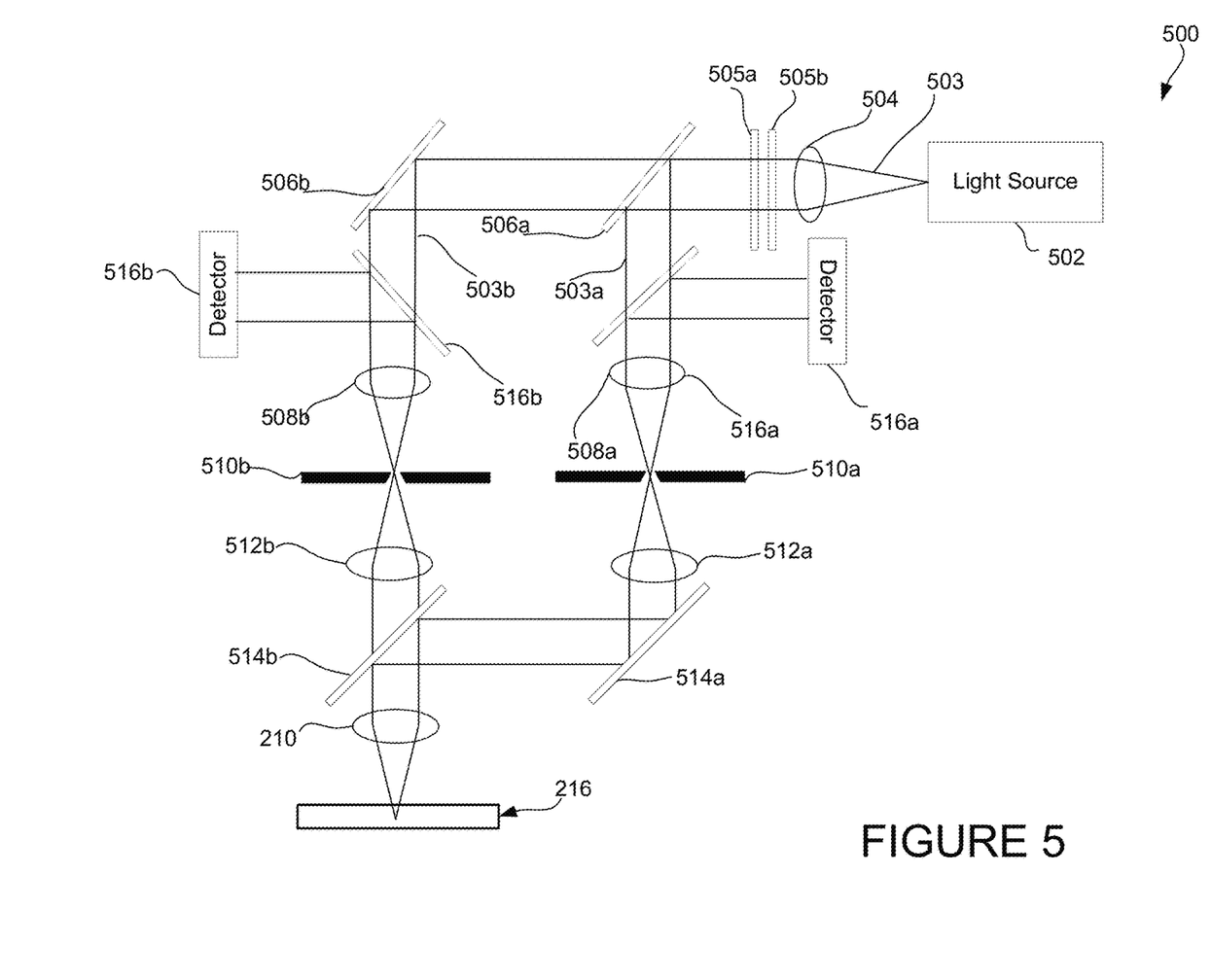
FIG. 5 is a diagrammatic representation of a combination inspection system in accordance with a specific implementation of the present invention.

FIG. 5 is a diagrammatic representation of a combination inspection system 500 in accordance with a specific implementation of the present invention. As shown, the system 500 includes a broadband light source (e.g., Xe arc lamp 502) for generating illumination light 503. The inspection system may include any suitable number and type of additional light sources, besides broadband light sources.

The illumination light 503 may then be collimated by lens 504. The collimated light may then be received by one or more optional filters or polarizers (e.g., 505a and 505b), which may be configured to filter out wavelengths over a maximum range or under a minimum range and/or polarize the illumination. The illumination light may then be received by wavelength bypass filters 506a and 506b that pass different wavelength bands for use in a defect inspection/review process. The system 500 may include any suitable optical elements for passing (or reflecting) two or more different wavelength bands along two different paths. In the illustrated system, a first spectral filter 506a is arranged to reflect a first illumination beam 503a at a first wavelength band and pass light at the other wavelengths to a second filter 506b. Similarly, second filter 506b is arranged to reflect a second illumination beam 503b at a second wavelength band. Any suitable number of spectral filters, including transmission filters, may be used to achieve different spectral bands.

A bypass filter may be implemented in any suitable form, such as the illustrated dichroic beam splitter 506a and 506b. For instance, dichroic prisms with dichroic optical coatings, which selectively reflect or transmit light depending on the light's wavelength, may be utilized in the system 500 to separate the illumination beam into two separate wavelength paths.

The two illumination beams 503a and 503b at the two different wavelengths are then passed through respective beam splitters 516a and 516b and focused via lenses 508a and 508b through respective aperture modules 510a and 510b and then collimated by lenses 512a and 512b. The two illumination beams are then recombined by mirrors 514a and 514b and focused at a particular depth of the multi-layer sample 216 via lens 210.

The combined output beam is then divided into its respective wavelength bands by dichroitic mirrors 514a and 514b. Each output beam at the two different wavelength bands are then directed through an output beam optical system (e.g., lens 512a and 512b, 508a and 508b, reflected from beam splitters 516a and 516b onto detectors 516a and 516b Additional spectral filters may be placed in each of the two spectrum paths and used to further define the spectrum of each beam. For example, one or more additional spectral filters can further be used to optimize the sensitivity of each path for the defects that are intended to be captured. A separate polarizing filter can also be positioned in each spectral path to further optimize the inspection sensitivity for each wavelength range. Further embodiments for achieving multiple wavelength bands are further described in U.S. application Ser. No. 14/078,271 filed 12 Nov. 2013 by Steven R. Lange, which application is incorporated herein by reference for the purpose of describing inspection tool features and techniques that can be combined with the confocal features and techniques of certain embodiments of the present invention.

Generally, each inspection wavelength range may be selected based on optimization of its sub-band, illumination and collection pupil aperture shapes, polarization of the illumination and collection path, magnification, pixel size, or any combination thereof.

For inspection of 3D stacks, different wavelength band pass ranges may be selected between about 700 nm and 950 nm to optimize the inspection sensitivity for the buried 3D defect types and/or material of the 3D structures. For instance, two long wavelength ranges may take the form of two narrow sub-bands that each has a width that is equal to or less than 50 nm. Along with a longer wavelength range, a shorter wavelength range, such as less than 400 nm, may also be used to inspect surface defects. In one embodiment, any suitable number of wavelength ranges may be selected between a deep ultraviolet (DUV) or UV range through a NIR range.

A polarization setting may also be applied to each wavelength range (or sub-band). For instance, a horizontal polarization may be selected for the selected longer wavelength sub-band. A polarization setting may be applied based on any suitable inspection parameter, such as defect type, sample composition, wavelength range or sub-band selection, etc.

Figure 6:
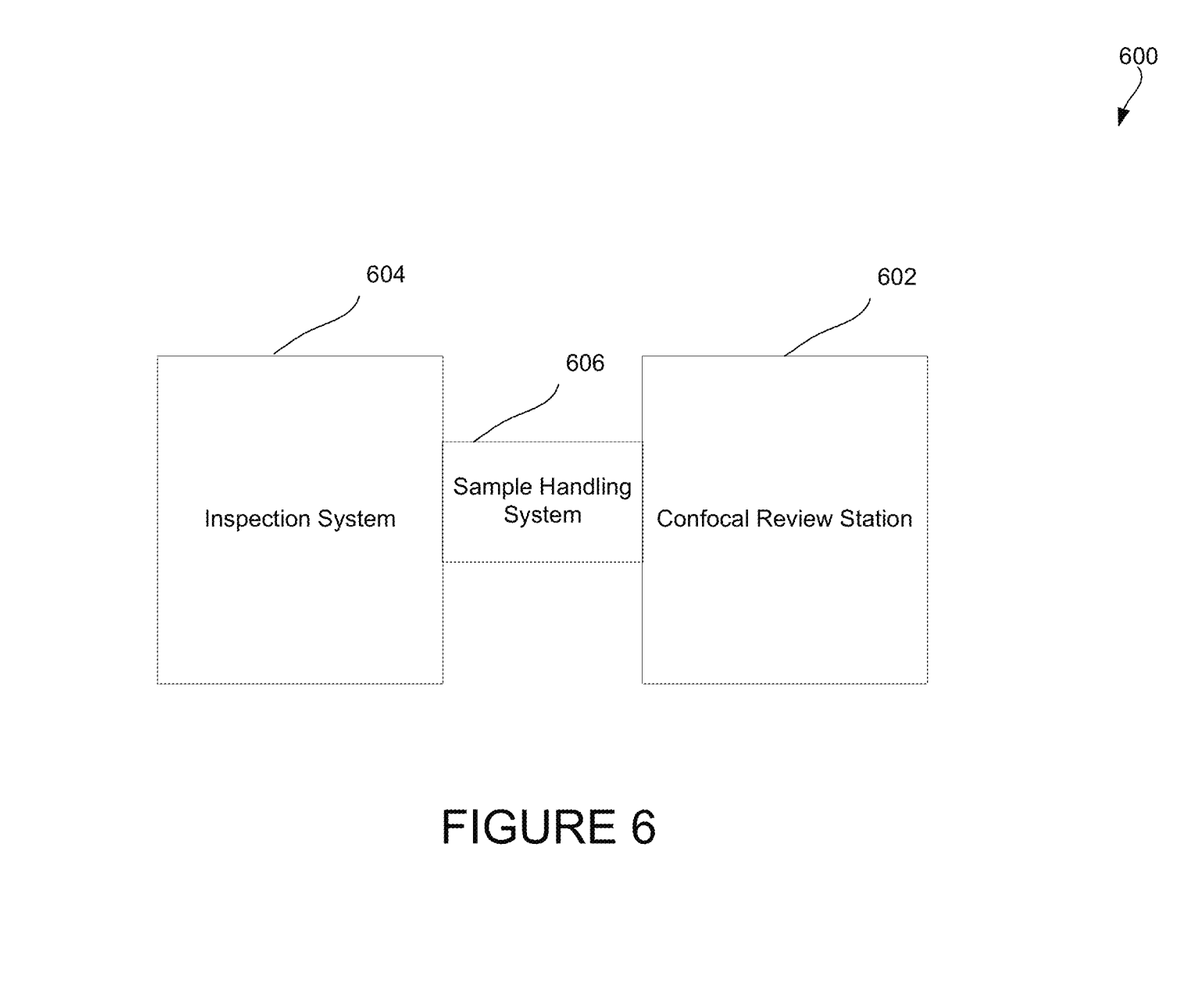
FIG. 6 is a diagrammatic representation of a system for inspecting and reviewing defects in accordance with one embodiment of the present invention.

FIG. 6 is a diagrammatic representation of a system 600 for inspecting and reviewing defects in accordance with one embodiment of the present invention. As shown, the system may include an inspector system 604 for finding defects using any type of inspection mode and does not have to include a confocal mode. The system 600 may also include a confocal review system 602 for reviewing defects that are found in 3D stack structures by the inspector 604. The system 600 may also include a sample handling system 606 for moving a sample, such as a wafer, from the inspector 604 to the review station 602.

Figure 7:
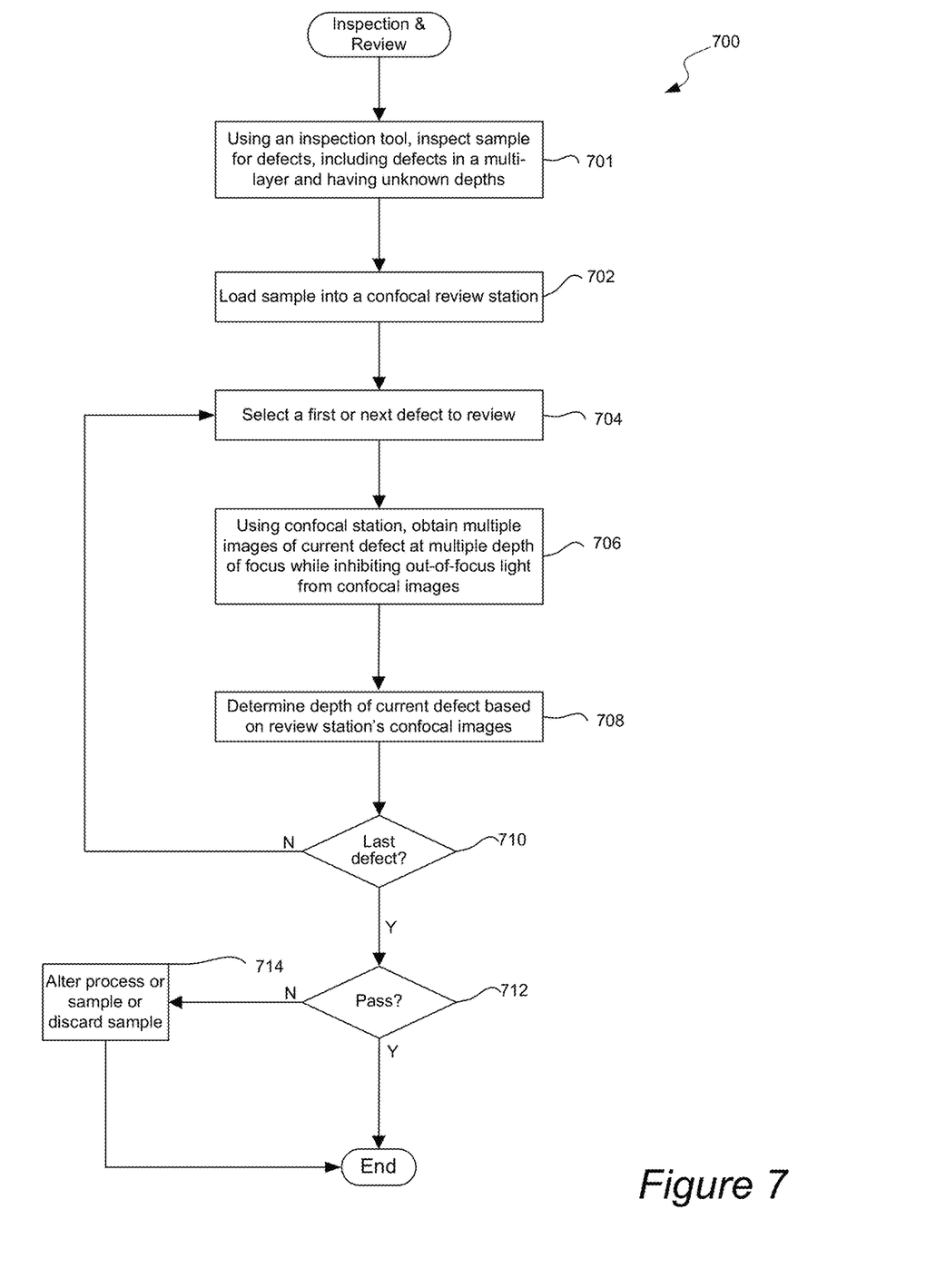
FIG. 7 is a flow chart illustrating an inspection and review process in accordance with an alternative embodiment of the present invention.

FIG. 7 is a flow chart illustrating an inspection and review process 700 in accordance with an alternative embodiment of the present invention. This combination process 700 may be implemented using separate inspection and review tools or a combinational system, such as the system of FIG. 6. Initially, a sample may be inspected for defects, including defects in a multi-layer and having an unknown depth, using an inspection tool (or module) in operation 701. For instance, a non-confocal inspection tool may be used to find defects and their general XY location, but not their depth location.

After defects are found, the sample may then be loaded into a confocal review station (or module) in operation 702. A first defect may then be selected for review in operation 704. For instance, a defect in a known 3D stack area may be selected for review.

Using the confocal station, multiple images of the current defect at multiple depth of focus may then be obtained, while inhibiting out-of-focus light from the images, in operation 706. That is, in-focus images of the defect area are obtained. One image that corresponds to the defect depth will have a sharper contrast than the other images. Accordingly, a depth of the current defect may be obtained based on the review station's confocal images in operation 708.

It may then be determined whether this is the last defect to review in operation 710. For instance, all the defects in 3D stacks may be reviewed. Of course, other types of defects may also be reviewed based on the images provided by the inspector tool. After the last defect is reviewed, it may then be determined whether the sample has passed inspection in operation 712. For instance, it determined whether the defects are yield-limiting defects or merely nuisance type defects. It may also be determined whether the defect is repairable. If the sample does not pass, the process or sample may be altered in operation 714. The sample may also be discarded, in addition to altering the process.

Certain embodiments of the present invention allow a high accuracy for finding the location of defects embedded in 3D stack structures. Additionally, some embedded defects, which are otherwise invisible to other high resolution inspection methods, may also be found using certain techniques of the present invention. Some embodiments may allow an improvement in the sensitivity.

Once the depth of defects is obtained, this information may be used to specify the configuration of the non-confocal inspection tool to be more or less sensitive to defects at certain depths or range of depths, for example, through polarization or multiple-wavelength selection (e.g., recipe setup and subsequent VENN analysis). Examples of such useful applications are further described in the above referenced U.S. application Ser. No. 14/078,271.

Any of the above described systems may include a controller configured (e.g., with programming instructions) to provide a user interface (e.g., on a computer screen) for displaying resultant test images and other inspection characteristics as described further herein. The controller may also be configured to receive the image or signal generated by each detector and analyze the resulting image or signal to determine whether defects are present on the sample, characterize defects present on the sample, or otherwise characterize the sample.

The controller may be any suitable combination of software and hardware. For example, the controller may include a processor, coupled to input/output ports, and one or more memories via appropriate buses or other communication mechanisms. The processor and memory may be programmed to implement instructions of the method embodiments of the present invention. The controller may also include one or more input devices (e.g., a keyboard, mouse, joystick) for providing user input, such as changing focus depths, viewing detection results data or images, setting up an inspection tool recipe.

Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

The optical layout of the confocal inspection/review tools can vary from that described above. For example, the objective lens can be one of many possible layouts, as long as the transmission coatings are optimized for the particular selected wavelength band or sub-band and the aberration over each waveband is minimized.

Certain embodiments of the present invention provide an inspection system that generates at least one light path at visible~NIR wavelengths. The system may also include components for optional polarized light in each illumination and collection path, optional spectral sub-band filters, and optional aperture shapes in the illumination and collection paths for the inspection of 3D wafer structures.

Any suitable lens arrangement may be used to direct the illumination beam towards the sample and direct the output beam emanating from the sample towards a detector. The illumination and collection optical elements of the system may be reflective or transmissive. The output beam may be reflected or scattered from the sample or transmitted through the sample.

It should be noted that the above description and drawings of an inspection system are not to be construed as a limitation on the specific components of the system and that the system may be embodied in many other forms. For example, it is contemplated that the inspection or measurement tool may have any suitable features from any number of known imaging or metrology tools arranged for detecting defects and/or resolving the critical aspects of features of a reticle or wafer. By way of example, an inspection or measurement tool may be adapted for bright field imaging microscopy, darkfield imaging microscopy, full sky imaging microscopy, phase contrast microscopy, polarization contrast microscopy, and coherence probe microscopy. It is also contemplated that single and multiple image methods may be used in order to capture images of the target. These methods include, for example, single grab, double grab, single grab coherence probe microscopy (CPM) and double grab CPM methods. Non-imaging optical methods, such as scatterometry, may also be contemplated as forming part of the inspection or metrology apparatus.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. For example, the defect detection characteristic data may be obtained from a transmitted, reflected, or a combination output beam. Additionally, the confocal system can be used at other wavelength ranges, besides visible to NIR, such as a visible, ultraviolet or deep-ultraviolet wavelength range, to determine depth of defects. Accordingly, the present embodiments are to be considered as illustrative and not restrictive, and the invention is not to be limited to the details given herein.

What is claimed is:

1. A method for inspecting a vertical stack structure, comprising:
   (a) on a confocal tool, repeatedly focusing an illumination beam at a same particular xy location and a plurality of focus planes at a plurality of different depths of a first vertical stack structure having a plurality of patterned layers, wherein the different depths correspond to incremental z positions from a top surface of the first vertical stack structure, through the plurality of patterned layers of the first vertical stack structure, and to a bottom of the first vertical stack structure, and wherein a defect is located at an unknown one of the different depths and the illumination beam has a wavelength range between about 700 nm and about 950 nm;
   (b) generating a plurality of in-focus images for the different depths based on in-focus output light detected from the first vertical stack structure at the different depths, wherein out-of-focus output light is inhibited from reaching the detector of the confocal system and inhibited from contributing to generation of the in-focus images; and
   (c) determining which one of the different depths at which the defect is located in the first vertical stack structure based on the in-focus images.

2. The method of claim 1, wherein the out-of-focus light is inhibited from reaching the detector of the confocal tool by an output aperture module that is positioned and dimensioned so as to block the out-of-focus output light at the wavelength range between about 700 nm and about 950 nm from reaching the detector.

3. The method of claim 1, wherein the defect was detected in the first vertical stack structure using another inspection tool that differs from the confocal tool, wherein such defect was detected without determining a depth of such defect with respect to the first vertical stack structure.

4. The method of claim 1, further comprising detecting the defect based on the in-focus images prior to determining which one of the different depths at which the defect is located in the first vertical stack structure based on the in-focus images.

5. The method of claim 1, wherein determining which one of the different depths at which the defect is located in the first vertical stack structure includes determining that a particular one of the in-focus images has a sharpest contrast and defining the particular in-focus image's corresponding depth as the depth of the defect.

6. The method of claim 1, further comprising determining a classification of the defect or discriminating a material of the defect based on the in-focus images.

7. The method of claim 1, further comprises:
on the confocal tool, repeatedly focusing one or more illumination beams at a second plurality of focus planes at a second plurality of different depths of each of a second plurality of vertical stack structures;
generating a second plurality of in-focus images for the second different depths based on in-focus output light detected from the second vertical stack structures at the second different depths, wherein out-of-focus output light is inhibited from reaching the detector of the confocal system and inhibited from contributing to generation of the second in-focus images; and
detecting one or more second defects in the second vertical stack structures; and
for each detected second defect, determining which one of the different depths at which the second defect is located based on the second in-focus images.

8. The method of claim 7, wherein a plurality of illumination beams are simultaneously focused at the second focus planes of the second vertical stack structures.

9. The method of claim 1, wherein the first vertical stack structure is a three-dimensional memory structure having a plurality of alternating patterned layers formed from an oxide material and either a nitride or polysilicon material.

10. A system for detecting defects or reviewing defects in a vertical semiconductor structure, the system comprising:
an illumination optics module for repeatedly focusing an illumination beam at a same particular xy location and a plurality of focus planes at a plurality of different depths of a first vertical stack structure having a plurality of patterned layers, wherein the different depths correspond to incremental z positions from a top surface of the first vertical stack structure, through the plurality of patterned layers of the first vertical stack structure, and to a bottom of the first vertical stack structure, and wherein a defect is located at an unknown one of the different depths and the illumination beam has a wavelength range between about 700 nm and about 950 nm;
a collection optics module for collecting in-focus output light from the plurality of different depths in response to the focused illumination beam that is focused at such different depths;
a detector for detecting the in-focus output light collected from the plurality of different depths, wherein the collection optics module is further arranged to inhibit out-of-focus output light from reaching the detector so as to inhibit such out-of-focus output light from contributing to generation of the in-focus images; and
a controller operable to perform the following operations:
generating a plurality of in-focus images for the different depths based on in-focus output light detected from the first vertical stack structure at the different depths; and
determining which one of the different depths at which the defect is located in the first vertical stack structure based on the in-focus images.

11. The system of claim 10, wherein the illumination optics module includes an illumination aperture module and the collection optics module includes an output aperture module.

12. The system of claim 11, wherein each of the illumination and output aperture modules is in the form of a fixed pinhole or slit array.

13. The system of claim 11, wherein each of the illumination and output aperture modules is in the form of a rotating Nipkow disk for scanning the focused illumination beam across a focal plane area of the sample.

14. The system of claim 11, wherein each of the illumination and output aperture modules is in the form of a programmable spatial modulator for scanning the focused illumination beam across a focal plane area of the sample.

15. The system of claim 11, wherein the illumination aperture module is positioned and dimensioned so as to block the out-of-focus output light at the wavelength range between about 700 nm and about 950 nm from reaching the detector.

16. The system of claim 10, wherein the illumination optics module includes one or more galvanic mirrors for scanning the focused illumination beam across a focal plane area of the sample.

17. The system of claim 10, wherein the defect was detected in the first vertical stack structure using another inspection tool that differs from the confocal tool, wherein such defect was detected without determining a depth of such defect with respect to the first vertical stack structure.

18. The system of claim 10, wherein the controller is further operable to detect the defect based on the in-focus images prior to determining which one of the different depths at which the defect is located in the first vertical stack structure based on the in-focus images.

19. The system of claim 10, wherein determining which one of the different depths at which the defect is located in the first vertical stack structure includes determining that a particular one of the in-focus images has a sharpest contrast and defining the particular in-focus image's corresponding depth as the depth of the defect.

20. The system of claim 10, wherein the controller is further operable to determine a classification of the defect or discriminate a material of the defect based on the in-focus images.

21. The system of claim 10, wherein the system is in the form of a confocal review module for reviewing defects, wherein the system further comprises an inspector module for detecting defects using a non-confocal inspection mode.

22. The system of claim 10, wherein the first vertical stack structure is a three-dimensional memory structure having a plurality of alternating patterned layers formed from an oxide material and either a nitride or polysilicon material.

* * * * *